(12) United States Patent
Sharpes

(10) Patent No.: US 12,357,487 B2
(45) Date of Patent: Jul. 15, 2025

(54) SPRING ENGAGEMENT AND DISENGAGEMENT DURING GAIT CYCLE

(71) Applicant: The Government of the United States, as represented by the Secretary of the Army, Washington, DC (US)

(72) Inventor: Nathan Sharpes, Abingdon, MD (US)

(73) Assignee: The Government of the United States, as represented by the Secretary of the Army, Washington, DC (US)

( * ) Notice: Subject to any disclaimer, the term of this patent is extended or adjusted under 35 U.S.C. 154(b) by 1463 days.

(21) Appl. No.: 16/795,622

(22) Filed: Feb. 20, 2020

(65) Prior Publication Data

US 2020/0268541 A1 Aug. 27, 2020

Related U.S. Application Data

(60) Provisional application No. 62/809,186, filed on Feb. 22, 2019.

(51) Int. Cl.
*A61H 3/00* (2006.01)
*A61F 5/01* (2006.01)
*A61H 1/02* (2006.01)

(52) U.S. Cl.
CPC .......... *A61F 5/0127* (2013.01); *A61F 5/0125* (2013.01); *A61H 1/0237* (2013.01);
(Continued)

(58) Field of Classification Search
CPC .................. A61F 5/0127; A61F 5/0125; A61F 2005/0197; A61F 5/01; A61H 1/0237;
(Continued)

(56) References Cited

U.S. PATENT DOCUMENTS 6,171,272 B1 * 1/2001 Akita .................... A61F 5/0127
602/27
6,929,614 B1 * 8/2005 Jackovitch ............ A61F 5/0127
602/27

(Continued)

FOREIGN PATENT DOCUMENTS

GB           2460039 A  * 11/2009  ......... A61F 5/0127
WO    WO-2018065615 A1 *  4/2018  ............... A61F 2/64
(Continued)

*Primary Examiner* — Timothy A Stanis
*Assistant Examiner* — Tyler A Raubenstraw
(74) *Attorney, Agent, or Firm* — Ronald Krosky

(57) ABSTRACT

Various embodiments that pertain to a joint-based spring configuration. The joint-based spring configuration can be employed during a gait cycle. A gait cycle can comprise a driven phase and a resetting phase. The driven phase can be when a foot is on the ground and the resetting phase can be when the foot is off the ground and moving to the next time the foot is on the ground. While the foot is on the ground a spring can be engaged such that it winds and unwinds. Conversely, when the foot is off the ground, the spring can be disengaged to allow a more natural movement for a wearer. The effects and timing of the winding/unwinding and disengagement of the spring combine to reduce a wear's energy expenditure over a gait cycle, reducing metabolic rate and fatigue.

1 Claim, 15 Drawing Sheets

(52) U.S. Cl.
CPC ............. *A61H 1/0266* (2013.01); *A61H 3/00* (2013.01); *A61F 2005/0197* (2013.01); *A61H 2201/164* (2013.01)

(58) Field of Classification Search
CPC .. A61H 1/0266; A61H 3/00; A61H 2201/164; A61H 2201/149; A61H 2201/1671; A61H 2205/088
See application file for complete search history.

(56) References Cited

U.S. PATENT DOCUMENTS

| | | | | |
|---|---|---|---|---|
| 7,410,471 | B1 * | 8/2008 | Campbell | A61F 5/0125 602/26 |
| 9,089,402 | B2 * | 7/2015 | Campbell | A61F 5/0127 |
| 9,398,970 | B1 * | 7/2016 | Meyer | A61F 5/0111 |
| 9,839,552 | B2 * | 12/2017 | Han | A61F 5/0127 |
| 9,962,279 | B2 * | 5/2018 | Haley | A43B 7/20 |
| 10,213,356 | B2 * | 2/2019 | Glaister | A61H 3/00 |
| 10,485,681 | B2 * | 11/2019 | Herr | A61F 2/70 |
| 10,512,774 | B2 * | 12/2019 | Dixon | A61H 3/00 |
| 10,576,620 | B1 * | 3/2020 | Chou | A61F 5/0102 |
| 10,874,539 | B2 * | 12/2020 | LeCursi | B29C 39/02 |
| 10,881,535 | B2 * | 1/2021 | Fujikake | A61F 2/6607 |
| 10,959,872 | B2 * | 3/2021 | Choi | A61H 1/0262 |
| 10,973,671 | B2 * | 4/2021 | Wang | A61F 5/0127 |
| 11,246,729 | B2 * | 2/2022 | Blanck | A61F 5/0111 |
| 11,278,434 | B2 * | 3/2022 | Kroll-Orywahl | A61F 5/01 |
| 11,324,655 | B2 * | 5/2022 | De Rossi | A61F 2/72 |
| 11,369,494 | B2 * | 6/2022 | Kazerooni | B25J 17/00 |
| 11,395,753 | B2 * | 7/2022 | LeCursi | A61F 5/0127 |
| 11,419,748 | B2 * | 8/2022 | Zelen | A61F 5/0195 |
| 2004/0015112 | A1 * | 1/2004 | Salutterback | A61F 5/0127 602/22 |
| 2004/0064195 | A1 * | 4/2004 | Herr | A61F 2/66 623/44 |
| 2006/0046907 | A1 * | 3/2006 | Rastegar | A63B 69/0028 482/148 |
| 2006/0185703 | A1 * | 8/2006 | Townsend | A61H 3/0277 135/82 |
| 2009/0306554 | A1 * | 12/2009 | Yasuie | A61H 3/008 601/5 |
| 2010/0113980 | A1 * | 5/2010 | Herr | A61H 3/00 600/587 |
| 2012/0209163 | A1 * | 8/2012 | Phillips | A61F 5/0102 602/23 |
| 2012/0283613 | A1 * | 11/2012 | DeHeer | A61F 5/0127 602/29 |
| 2012/0289870 | A1 * | 11/2012 | Hsiao-Wecksler | A61H 3/00 601/5 |
| 2013/0046218 | A1 * | 2/2013 | Wiggin | A61F 5/0127 602/16 |
| 2013/0190669 | A1 * | 7/2013 | Rokosz | A61F 5/0125 602/16 |
| 2013/0296746 | A1 * | 11/2013 | Herr | A63B 23/0405 601/34 |
| 2014/0109443 | A1 * | 4/2014 | Fanchiang | A61F 5/0127 36/140 |
| 2014/0276304 | A1 * | 9/2014 | Dollar | A61F 5/0102 602/16 |
| 2014/0308065 | A1 * | 10/2014 | DeHarde | F16F 1/10 403/113 |
| 2014/0330431 | A1 * | 11/2014 | Hollander | A61H 3/00 29/428 |
| 2015/0321342 | A1 * | 11/2015 | Smith | A61H 3/00 74/490.03 |
| 2016/0015545 | A1 * | 1/2016 | Petursson | A61F 5/0193 602/16 |
| 2016/0113831 | A1 * | 4/2016 | Hollander | A61H 3/00 623/32 |
| 2016/0270944 | A1 * | 9/2016 | Bean | A61F 5/0125 |
| 2016/0374844 | A1 * | 12/2016 | DeHarde | F16F 15/04 602/16 |
| 2016/0374887 | A1 * | 12/2016 | Wu | A61F 2/64 623/31 |
| 2017/0135841 | A1 * | 5/2017 | Bonutti | A61F 5/0127 |
| 2017/0231797 | A1 * | 8/2017 | LeCursi | A61F 5/0125 602/16 |
| 2017/0340506 | A1 * | 11/2017 | Zhang | A61H 3/00 |
| 2018/0161188 | A1 * | 6/2018 | Zistatsis | A61H 1/024 |
| 2018/0177672 | A1 * | 6/2018 | Uchida | A61H 1/0237 |
| 2018/0280178 | A1 * | 10/2018 | Shimada | B25J 9/1045 |
| 2018/0289524 | A1 * | 10/2018 | Takeda | A61F 5/0127 |
| 2018/0344561 | A1 * | 12/2018 | Komatsu | A61H 1/024 |
| 2019/0216627 | A1 * | 7/2019 | Requa | A61F 5/01 |
| 2019/0298564 | A1 * | 10/2019 | Van Der Wilk | A61F 5/0127 |
| 2020/0397601 | A1 * | 12/2020 | Smith | B25J 17/0241 |

FOREIGN PATENT DOCUMENTS

| | | | | |
|---|---|---|---|---|
| WO | WO-2019164633 | A2 * | 8/2019 | ....... A63B 21/00069 |
| WO | WO-2020018035 | A2 * | 1/2020 | ........... A61F 5/0127 |
| WO | WO-2020039063 | A1 * | 2/2020 | ........... A61F 2/6607 |

* cited by examiner

SPRING ENGAGEMENT AND DISENGAGEMENT DURING GAIT CYCLE

CROSS-REFERENCE

This application claims priority to U.S. Provisional Patent Application No. 62/809,186 filed on Feb. 22, 2019. U.S. Provisional Patent Application No. 62/809,186 is incorporated by reference in this application.

GOVERNMENT INTEREST

The innovation described herein may be manufactured, used, imported, sold, and licensed by or for the Government of the United States of America without the payment of any royalty thereon or therefor.

BACKGROUND

As a person walks, they can expend energy. How much energy they expend can be based on a number of different factors. For example, walking up an incline as well as a high environmental temperature can cause an increased in expended energy over walking on flat terrain with an average environmental temperature. Increased expending of energy can be considered to be a negative aspect and therefore it can be beneficial to lower an amount of energy expended.

SUMMARY

In one embodiment, a wearable energy system comprises a spring and a coupling mechanism. The coupling mechanism can be configured to couple the spring to a wearer of the spring such that the spring moves with a joint of the wearer. The spring can be engaged during a stance phase of a gait cycle of the wearer. The spring can be disengaged during a swing phase of the gait cycle of the wearer.

In another embodiment, a system comprises a housing with a spring and a foot component. The housing with the spring can be configured to be worn by a user. The foot component can be configured to sense when a foot of the user is on a ground during a gait cycle of the user and when the foot of the user is not on the ground during the gait cycle.

In yet another embodiment, a method can comprise winding a spring associated with a joint of a wearer during a dorsiflection/flexion portion of a stance phase of a gait cycle. The method can also comprise unwinding the spring associated with the joint of the wearer during a plantarflection/extension portion of the plant phase of the gait cycle.

BRIEF DESCRIPTION OF THE DRAWINGS

Incorporated herein are drawings that constitute a part of the specification and illustrate embodiments of the detailed description. The detailed description will now be described further with reference to the accompanying drawings as follows.

DETAILED DESCRIPTION

Figure 9A:
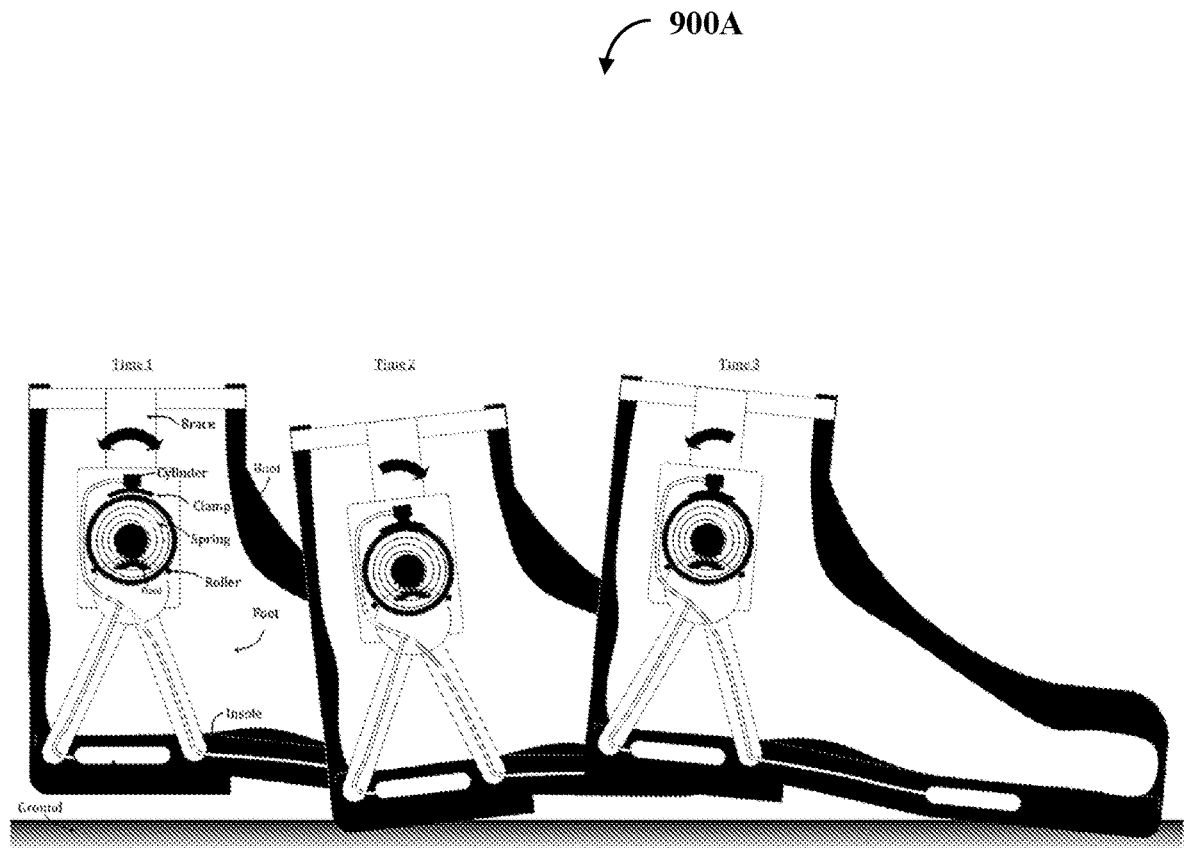
FIG. 9A illustrates a first embodiment of a step sequence.

A spring can be worn by a user along a leg joint (e.g., ankle, knee, or hip); and the spring can be coupled to the user by an ankle, knee, or hip coupling band mechanism such as the one shown in FIG. 9A. As the user walks as part of their normal gait cycle, the spring can be wound and then unwound. When the spring is unwound, energy can be returned to the gait cycle and thus the metabolic rate can be lower.

Further, the spring can function to be engaged during part of the gait cycle and disengaged for another part of the gait cycle. When a foot of the user is planted, the spring can be engaged such that the spring winds and unwinds. When the foot is not planted, the spring can be disengaged such that the spring neither winds nor unwinds.

The following includes definitions of selected terms employed herein. The definitions include various examples. The examples are not intended to be limiting.

"One embodiment", "an embodiment", "one example", "an example", and so on, indicate that the embodiment(s) or example(s) can include a particular feature, structure, characteristic, property, or element, but that not every embodiment or example necessarily includes that particular feature, structure, characteristic, property, or element. Furthermore, repeated use of the phrase "in one embodiment" may or may not refer to the same embodiment.

"Computer-readable medium", as used herein, refers to a medium that stores signals, instructions and/or data. Examples of a computer-readable medium include, but are not limited to, non-volatile media and volatile media. Non-volatile media may include, for example, optical disks, magnetic disks, and so on. Volatile media may include, for example, semiconductor memories, dynamic memory, and so on. Common forms of a computer-readable medium may include, but are not limited to, a floppy disk, a flexible disk, a hard disk, a magnetic tape, other magnetic medium, other optical medium, a Random Access Memory (RAM), a Read-Only Memory (ROM), a memory chip or card, a memory stick, and other media from which a computer, a processor or other electronic device can read. In one embodiment, the computer-readable medium is a non-transitory computer-readable medium.

"Component", as used herein, includes but is not limited to hardware, firmware, software stored on a computer-readable medium or in execution on a machine, and/or combinations of each to perform a function(s) or an action(s), and/or to cause a function or action from another component, method, and/or system. Component may include a software controlled microprocessor, a discrete component, an analog circuit, a digital circuit, a programmed logic device, a memory device containing instructions, and so on. Where multiple components are described, it may be possible to incorporate the multiple components into one physical component or conversely, where a single component is described, it may be possible to distribute that single component between multiple components.

"Software", as used herein, includes but is not limited to, one or more executable instructions stored on a computer-readable medium that cause a computer, processor, or other electronic device to perform functions, actions and/or behave in a desired manner. The instructions may be embodied in various forms including routines, algorithms, modules, methods, threads, and/or programs, including separate applications or code from dynamically linked libraries.

Figure 1:
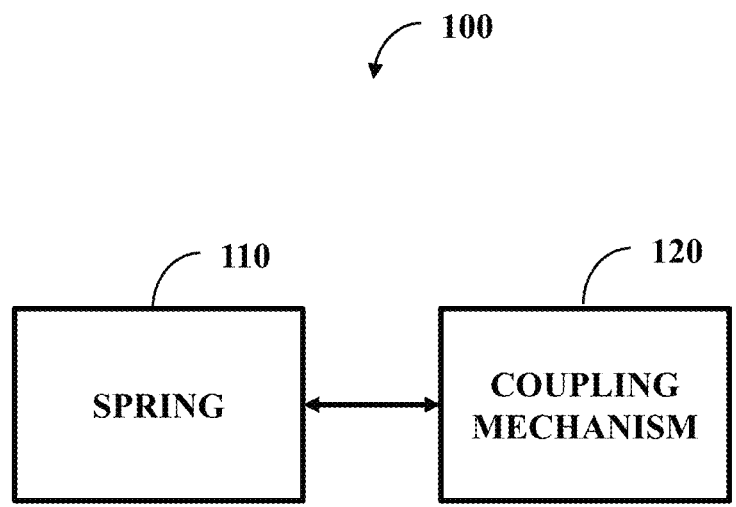
FIG. 1 illustrates one embodiment of a system comprising a spring and a coupling mechanism.

FIG. 1 illustrates one embodiment of a system 100 comprising a spring 110 and a coupling mechanism 120. The spring and coupling mechanism can be part of a wearable energy system, such as an apparatus configured for attachment with a boot and/or part of the boot itself. The coupling mechanism 120 can be configured to couple the spring 110 to a wearer of the spring 110 such that the spring 110 moves with a joint of the wearer. Example joints can be an ankle joint, a knee joint, or a hip joint with the spring 110 physically aligning with the respective joint of the wearer.

The wearer can experience a gait cycle as they walk. This gait cycle can comprise two portions—a swing phase and a stance phase. The swing phase can be when the foot of the wearer is off the ground while the stance phase can be when the foot is on the ground.

The spring 110 can be disengaged when the foot is off the ground, allowing the foot and leg to move freely without significant resistance from the spring. This way, during the swing phase, the metabolic rate of the wearer is not significantly increased over normal operation. During the stance phase, the spring 110 can be engaged so the spring can be wound and unwound.

The stance phase comprises a first portion and a second portion, with the second portion following the first portion in time. The first portion can be where the spring 110 is wound and the second portion can be when the spring 110 is unwound. As the wearer steps down and places force on the ground, in response the coupling mechanism 120 engages and the spring 110 can be wound. As the wearer lifts up and pushes from the ground, in response the spring can be unwound. As such, when the spring 110 is unwound, energy is returned into the gait cycle lowering the metabolic rate of the wearer.

In one example, the coupling mechanism 120 can align the spring 110 with an ankle joint of the wearer. The first portion can comprise a period when the leg and foot are less than 90 degrees and this can be when the spring 110 is wound due to rooting the foot. The second portion can comprise a period when the leg and foot are greater than 90 degrees and this can be when the spring 110 is unwound due to push-off of the foot.

Figure 2:
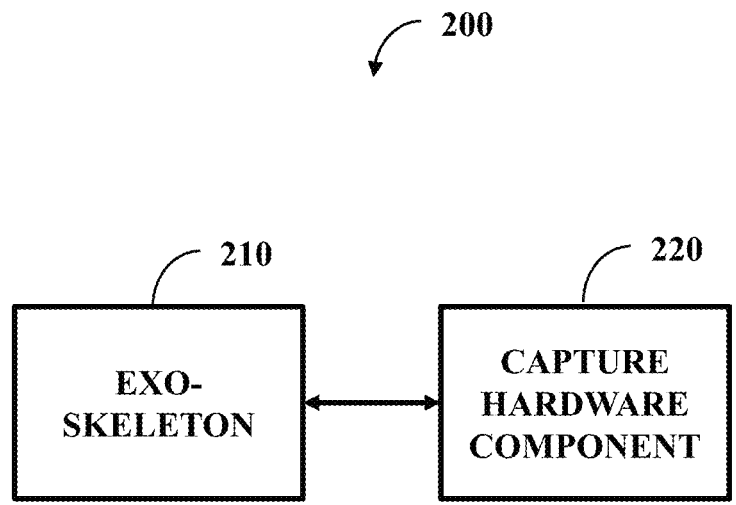
FIG. 2 illustrates one embodiment of a system comprising an exoskeleton and a capture hardware component.

FIG. 2 illustrates one embodiment of a system 200 comprising an exoskeleton 210 and a capture hardware component 220. The exoskeleton 210 can attach to the boot of the wearer and comprise the spring 110 of FIG. 1 and the coupling mechanism 120 of FIG. 1. The capture hardware component 220 can be part of the boot and be configured to utilize pressure from the wearer's bodyweight against the boot/ground. Engagement and disengagement of the spring 110 of FIG. 1 can be managed by the capture hardware component 220 such that the capture hardware component 220 utilizes stance pressure to engage the spring 110 of FIG. 1 and the capture hardware component 220 does not utilize stance pressure when the spring 110 of FIG. 1 is disengaged. With this, when the leg is freely swinging, the spring 110 of FIG. 1 can be disengaged. Meanwhile, when the leg is planted, the spring 110 of FIG. 1 can be engaged.

Figure 3:
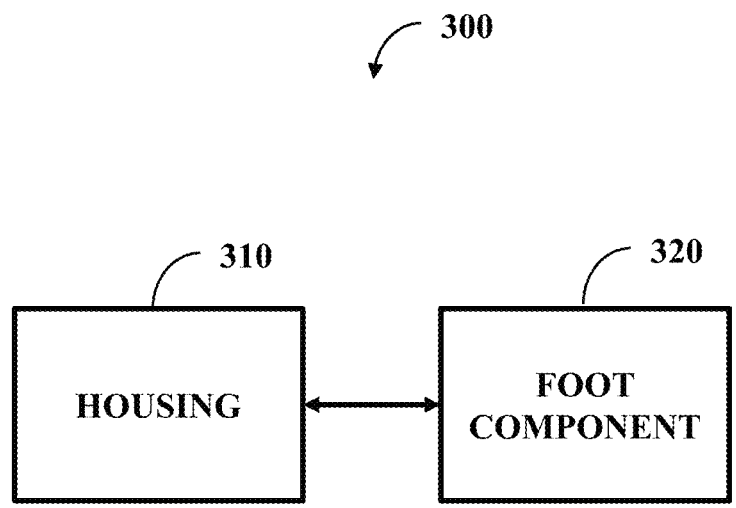
FIG. 3 illustrates one embodiment of a system comprising a housing and a foot component.

FIG. 3 illustrates one embodiment of a system 300 comprising a housing 310 and a foot component 320. The housing 310 can retain the spring 110 of FIG. 1 and be worn by a user (e.g., the housing being at least part of the exoskeleton 210 of FIG. 2). The foot component 320 can be configured to sense when a foot of the user is on a ground during a gait cycle of the user and when the foot of the user is not on the ground during the gait cycle. In one example, the foot component 320 resides in a bottom of a shoe (e.g., boot).

The housing 310 can retain a clamp component configured to cause the spring 110 of FIG. 1 to be engaged in response to the foot component 320 sensing that the foot of the user is on the ground during the gait cycle. Similarly, the clamp component can be configured to cause the spring 110 of FIG. 1 to be disengaged in response to the foot component not sensing that the foot of the user is on the ground during the gait cycle. When the foot is on the ground, there can be a first phase when the spring is wound and a subsequent second phase when the spring is unwound.

The housing 310 can be coupled to a joint of the wearer, such as the ankle joint or knee joint. The spring 110 of FIG. 1, when part of the housing 310, can be wound due to user dorsiflection in a leg associated with the joint and the spring is unwound in response plantarflection in the leg associated with the joint. The spring 110 of FIG. 1 being unwound can provide energy to the ankle joint for the gait cycle during the second phase.

Figure 4:
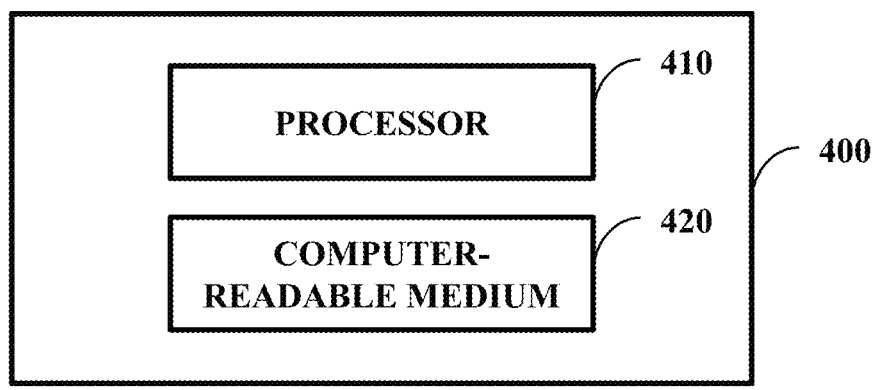
FIG. 4 illustrates one embodiment of a system comprising a processor and a computer-readable medium.

FIG. 4 illustrates one embodiment of a system 400 comprising a processor 410 and a computer-readable medium 420 (e.g., non-transitory computer-readable medium). In one embodiment, the computer-readable medium 420 is communicatively coupled to the processor 410 and stores a command set executable by the processor 410 to facilitate operation of at least one component disclosed herein (e.g., the clamp component as discussed above). In one embodiment, at least one component disclosed herein (e.g., the foot component 320 of FIG. 3) can be implemented, at least in part, by way of non-software, such as implemented as hardware by way of the system 400. In one embodiment, the computer-readable medium 420 is configured to store processor-executable instructions that when executed by the processor 410, cause the processor 410 to perform at least part of a method disclosed herein (e.g., at least part of one of the methods 500-600 discussed below).

Figure 5:
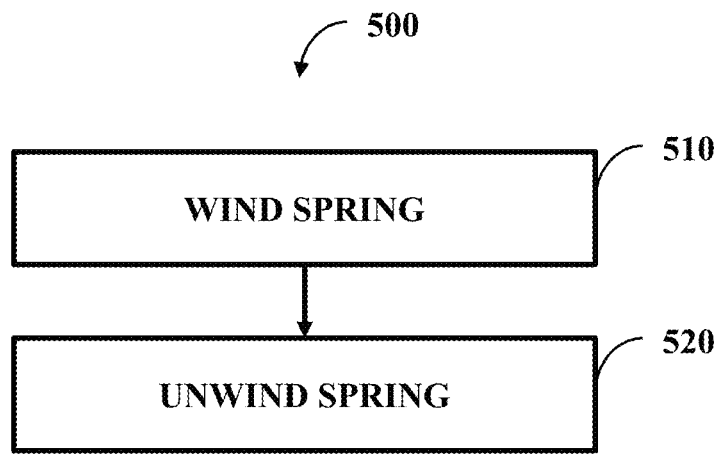
FIG. 5 illustrates one embodiment of a method comprising two actions.

FIG. 5 illustrates one embodiment of a method 500 comprising two actions 510-520. At 510, there can be winding of a spring associated with a joint (e.g., knee, ankle, or hip) of a wearer during a dorsiflection portion of the stance phase of the gait cycle for the ankle or flexion of the knee or hip. At 520, unwinding of the spring associated with the joint of the wearer can occur during a plantarflection portion of the stance phase of the gait cycle for the ankle or extension of the knee or hip.

Figure 6:
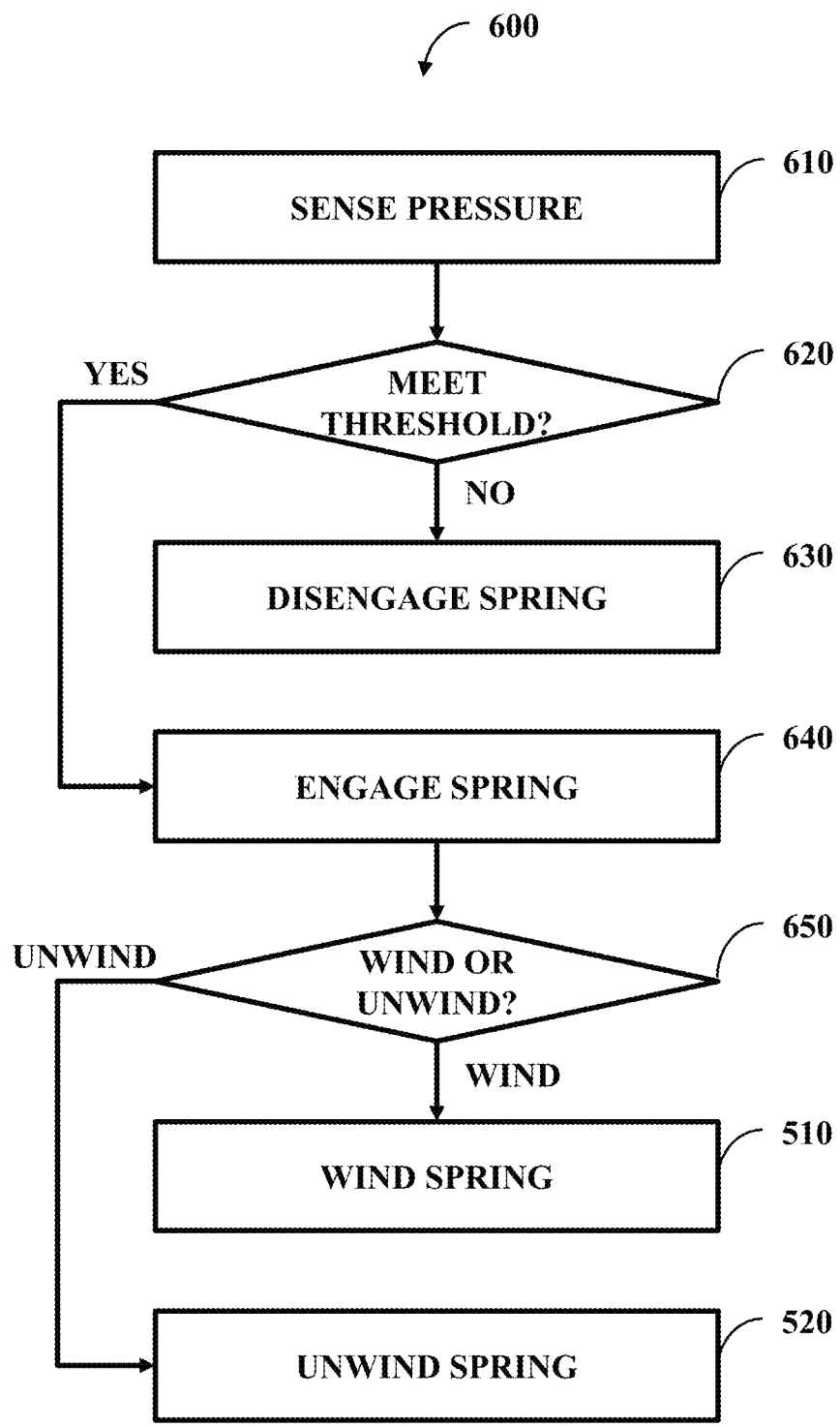
FIG. 6 illustrates one embodiment of a method comprising seven actions.

FIG. 6 illustrates one embodiment of a method 600 comprising seven actions 610-650 and 510-520. At 610, a pressure can be sensed, such as by the foot component 320 of FIG. 3. This sensed pressure can be compared against a threshold at 620 to determine if the pressure meets a threshold. In one example, the threshold can be about zero. If there is a pressure, then the foot component can sense that the wearer is experiencing a stance phase of the gait cycle and if there is not a pressure, then the foot component can sense that the wearer it experiencing a swing phase of the gait cycle. Therefore, sensing if the wearer is experiencing the stance phase or the swing phase can be based on determining if the pressure meets the threshold (e.g., surpasses the threshold or at least equals the threshold.

Returning to the example where the threshold is about zero, when there is no pressure, the determination can be that the wearer is in the swing phase. Therefore, the method can go to 630 where the mechanism is caused to disengage the spring 110 of FIG. 1 so to prevent winding and encumbering the wearer during motions of little natural work by a joint. When there is pressure, the determination can be that the wearer is in the stance phase. Therefore, the method can go to 640 where the mechanism is caused to engage the spring 110 of FIG. 1 so to effectuate winding and unwinding supporting and aiding a joint during stance phase.

At 650, a check can occur on if the spring 110 of FIG. 1 should be wound or unwound—winding can occur at 510 and unwinding can occur at 520. The check 650 can be a physical response of the spring 110 of FIG. 1 to movement of a joint (e.g., ankle or knee) of the wearer. When the joint moves in response to the dorsiflection or flexion portion, then the spring 110 of FIG. 1 can wind at 510. Conversely, when the joint moves in response to the plantarflection or extension portion, then the spring 110 of FIG. 1 can unwind at 520.

While the methods disclosed herein are shown and described as a series of blocks, it is to be appreciated by one of ordinary skill in the art that the methods are not restricted by the order of the blocks, as some blocks can take place in different orders.

For a gait cycle or other work cycle, there can be periods of positive work, negative work, and no work conditions. In the context of the ankle in human locomotion, positive work can be propulsion (e.g., work done to push the body forward). Negative work can be work done to support the body (e.g., work that does not contribute or exists in opposition to propulsion, work done during early stance phase, etc.) No work can be the negligible work done when the leg is in the air, as during swing phase. This work is performed by the various muscles of the leg and count toward the total metabolic expenditure of the body. If portions of either the positive or negative work can be performed by an exoskeleton, then the metabolic expenditure associated with gait will be reduced.

To perform this work, such as mechanically with an exoskeleton, it can be desirable to transfer force in one (driven) phase, while having no load on the source (body) in another (resetting) phase. For the case of the ankle joint, the driving motion is when the foot is on the ground and dorsial- and plantar flexion occur, while the resetting motion is the swing phase. To accomplish this operation, the exoskeleton's mechanism can perform work during the driven motion, but physically disconnect during the resetting motion, so as to not impart forces during swing phase when negligible work is done, and reconnecting during the next subsequent driven motion.

Physical disconnect can be accomplished using a ratchet or one-way clutch. However, this type of solution may be limited, such that is can only allow unidirectional unencumbered motion while disconnected. This can be problematic since the motion of the ankle during swing phases is bi-directional. Furthermore, a ratchet can generate a great deal of noise and this can be less than desirable for the wearer. To allow for bi-directional motion during disconnect while also having a desirable noise level, a clutch can be employed. This can introduce a break in the drivetrain. However, a clutch can have its own difficulties such that it can be difficult to execute in a small physical dimension. Therefore, it can be advantageous to have a way to keep the drivetrain physically connected at all times to the coupling mechanism 120 of FIG. 1 (e.g., exoskeleton brace), but still be able to not impart force on the body during a reset type motion (even a bi-directional resetting motion).

In one embodiment, the spring 110 of FIG. 1 is fixed at one end and free to move at the other. In this way, when the free end of the spring 110 of FIG. 1 is displaced, it stores energy proportional to the displacement of the spring 110 of FIG. 1. The spring 110 of FIG. 1 can be constrained at one end by a foot-pressure-actuated clamp (e.g., by way of the foot component), and displacement is input from the rotation of the ankle joint. Because of the motion of the ankle joint (dorsiflexion), the spring 110 of FIG. 1 is displaced (either linearly or rotationally) storing energy (negative work). As the gait cycle progresses to push off (plantarflexion), the spring 110 of FIG. 1 displaces the opposite direction, releasing the stored energy back to ankle joint (positive work). When the foot is then off the ground, the motion of the ankle is bi-directional, which is allowed by the mechanism with negligible torque to make this resetting move, as the spring 110 of FIG. 1 is not clamped, allowing it to move/rotate as a rigid body. With this mechanism, a portion of the negative work of gait is performed for the body by storing energy in the spring 110 of FIG. 1. This energy is then released, performing a portion of the positive work of gait cycle. The mechanism then is disengaged during the no work phase of gait (swing phase). Reducing both the negative and positive work the body performs for gait cycle reduces the metabolic expenditure for movement, ultimately decreasing fatigue.

Figure 7:
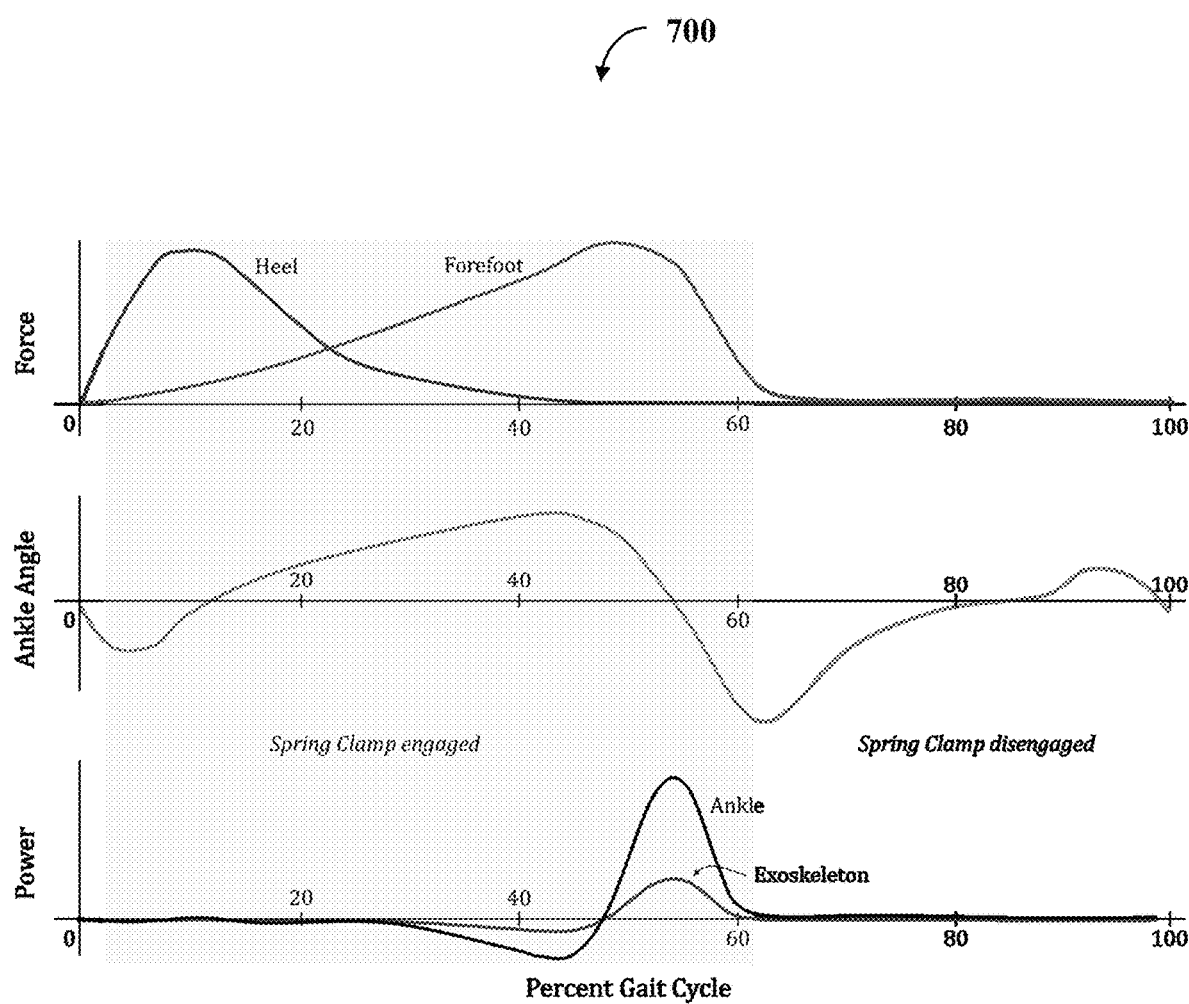
FIG. 7 illustrates one embodiment of an ankle-based graph set.

FIG. 7 illustrates one embodiment of an ankle-based graph set 700. The top graph illustrates force of the heel and forefoot during a gait cycles with the gait cycle beginning at heel strike. The middle graph illustrates ankle angle (where zero degrees is the shank perpendicular to the foot). The bottom graph illustrates quantitative ankle power, angle angle, and force on the heel and forefoot sections of the foot during a gait cycle, where the gait cycle begins at heel strike. Also shown in the shaded portion of the graph is the period of engagement for the spring clamp (e.g., to about sixty-two percent gait cycle) and subsequent exoskeleton influence (e.g., from about sixty-two percent gait cycle).

For the ankle angle graph, 0 is used when the foot and leg are perpendicular so so normalize the 90 degree designation. So The ankle angle of the graph set 700 is at value 0 for 90 degrees and then plotted against time. For the power and force graphs, these are value plotted against time as well, normalized to one gait cycle.

Figure 8A:
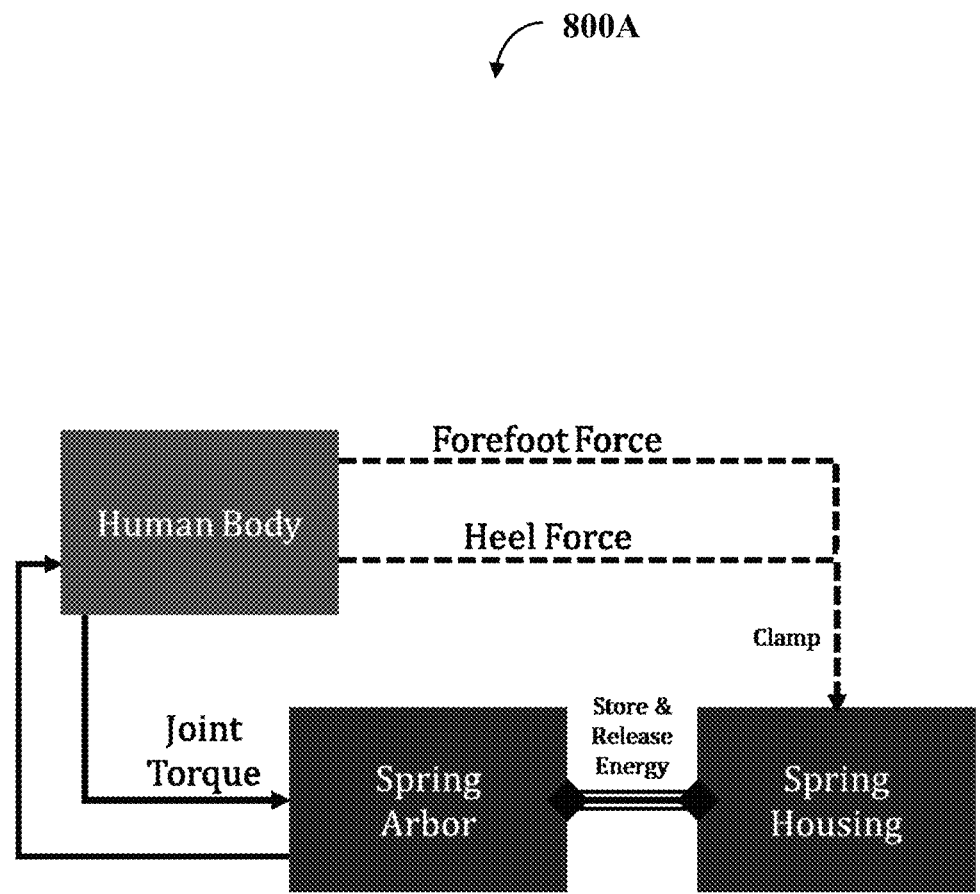
FIG. 8A illustrates a first embodiment of an environment comprising a spring arbor and a spring housing that interact with a human body.

FIG. 8A illustrates a first embodiment of an environment 800A where a spring arbor (center part of the spring) and a spring housing that interact with a human body. Different embodiments can be practiced, such as the spring arbor and spring housing combining to form the spring. In the environment 800A energy flows through from the human body to the exoskeleton mechanism (that retains the spring arbor and spring housing) and back to the body. Forces (e.g., pressure) from the foot can be employed from the body during the gait cycle to control the actuation of a spring clamp and subsequently store and release of energy in the spring. In this embodiment, joint torque turns the spring arbor and the spring clamp holds the spring housing stationary, allowing energy to be stored/released.

Figure 8B:
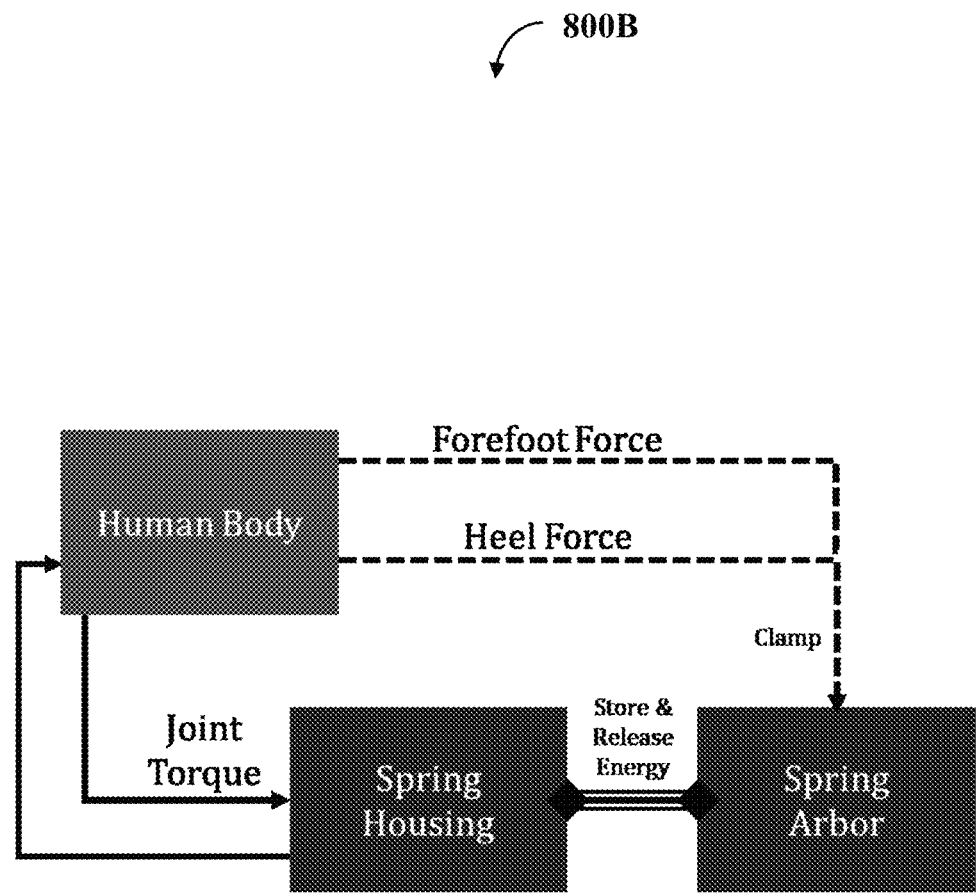
FIG. 8B illustrates a second embodiment of an environment where the spring arbor and the spring housing that interact with the human body.

FIG. 8B illustrates a second embodiment of an environment 800B where the spring arbor and the spring housing that interact with the human body. In contrast to the environment 800A, here joint torque turns the spring housing and the spring clamp holds the spring arbor stationary, allowing energy to be stored/released.

FIG. 9A illustrates a first embodiment of a step sequence 900A. The sequence comprises three times—time 1, time 2, and time 3. Time 2 follows Time 1, Time 3 follows Time 2, and a repeat of Time 1 occurs after Time 3. Time 1 is when the boot is off the ground, Time 2 is during heel strike, and Time 3 is during push-off (heel-lift pressure on forefoot).

The step sequence 900A shows clamp actuation in response to pressure from the foot against the boot/ground. When the foot is off the ground the clamp does not make contact with the spring (housing/arbor depending on embodiment). However, when the foot is on the ground the clamp holds the spring (housing/arbor depending on embodiment). In this embodiment, pressure from filled bladders (e.g. foot component) under the heel and forefoot apply pressure to a cylinder, pressing a clamp again the spring 110 of FIG. 1 (housing/arbor depending on embodiment), holding it stationary and allowing energy to be stored and released from/to the spring/exoskeleton brace. The bladders can be filled with a liquid, such as oil, and function as a hydrolic cylinder. The bladder can be filled with a non-liquid (e.g., air), but it can be desirable in at least some embodiments to use a non-compressible liquid.

Figure 9B:
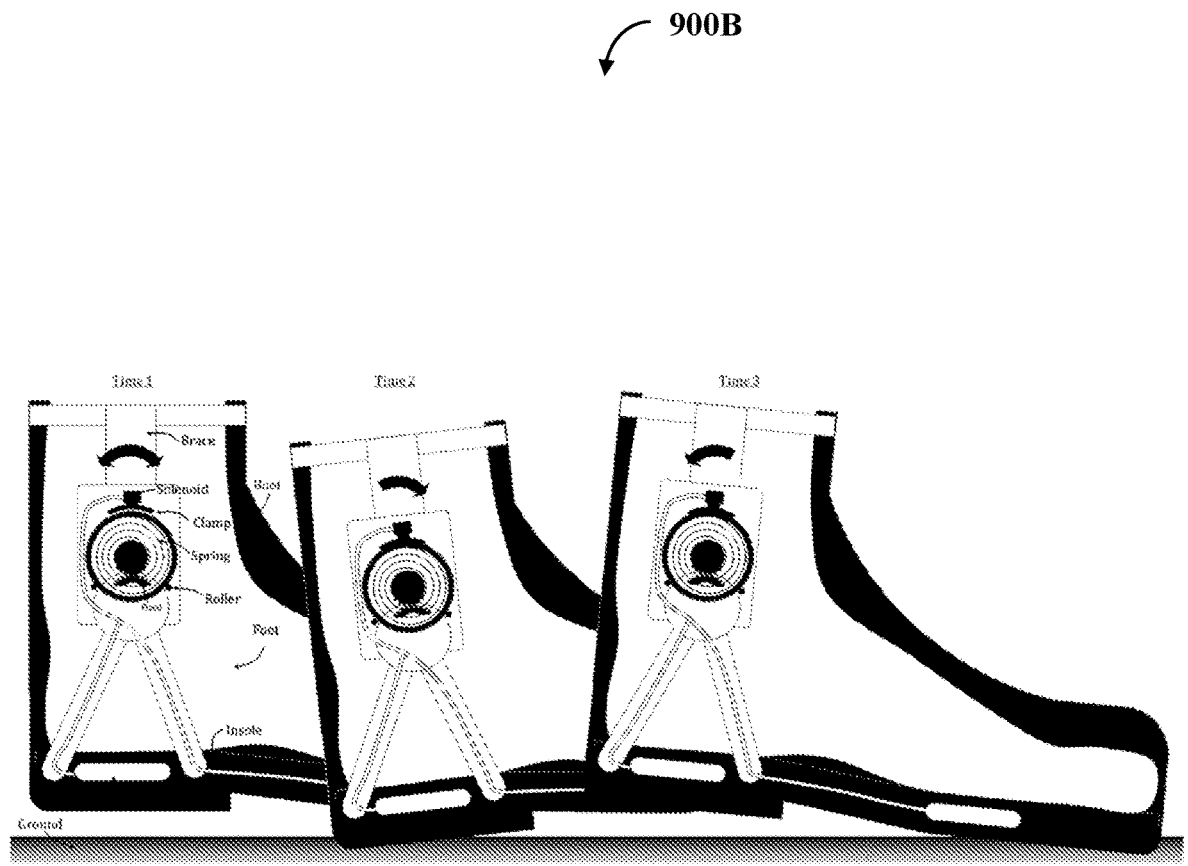
FIG. 9B illustrates a second embodiment of a step sequence.

FIG. 9B illustrates a second embodiment of a step sequence 900B. Here, instead of the bladders of FIG. 9A, the foot component implements as a pressure sensor set. A signal from pressure sensors under the heel and forefoot send a signal to a solenoid, pressing a clamp again the spring 110 of FIG. 1 (housing/arbor depending on embodiment), holding it stationary and allowing energy to be stored and released from/to the spring/exoskeleton brace.

Figure 10:
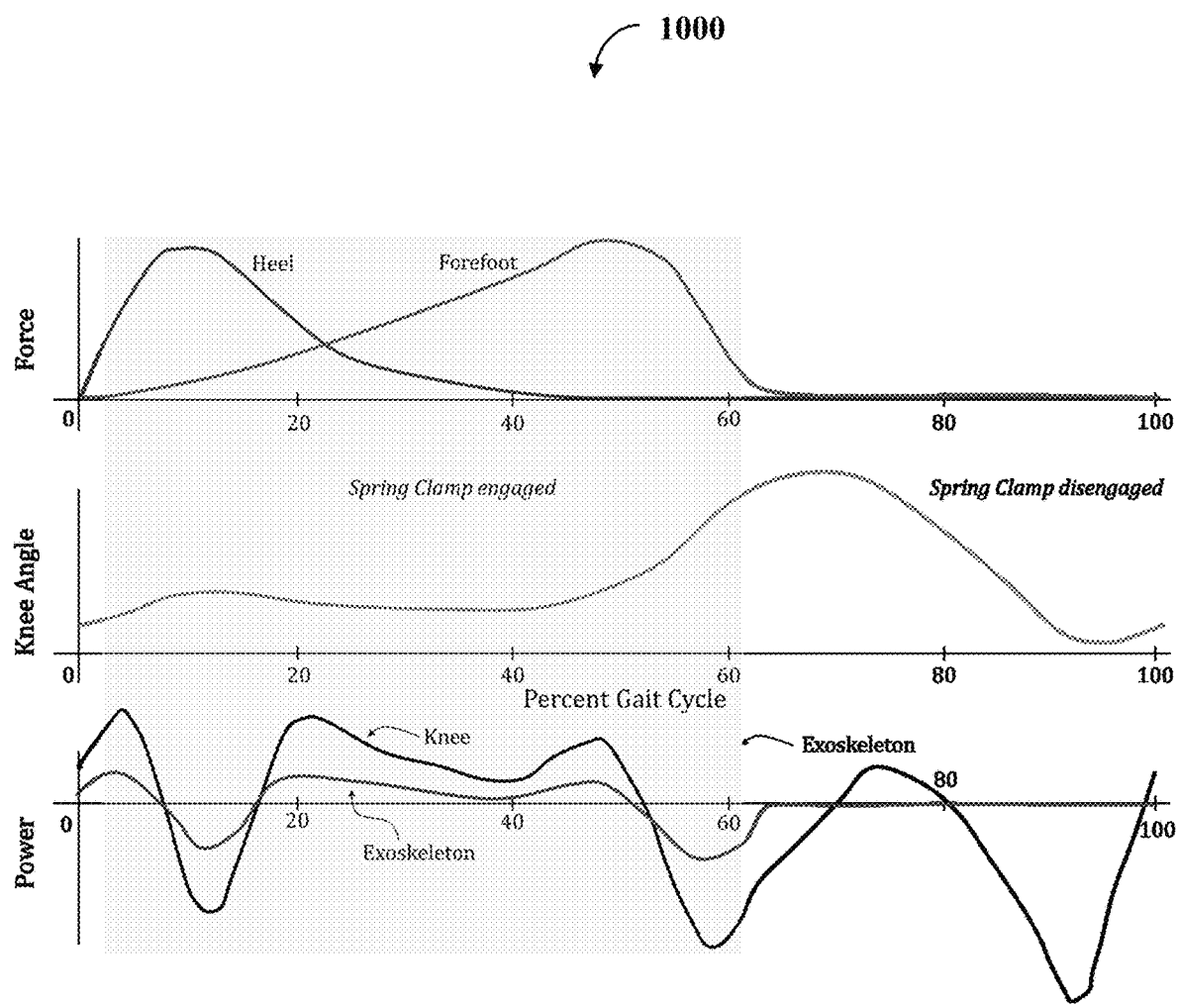
FIG. 10 illustrates one embodiment of a knee-based graph set.

FIG. 10 illustrates one embodiment of a knee-based graph set 1000. As discussed above, while FIGS. 7-9B address the ankle joint, aspects disclosed herein can be practiced with other leg joints, such as the knee or hip. For FIG. 10 (and FIGS. 11A-11B below), this can be the knee joint. Quantitative knee power, knee angle (where zero degrees is the shank colinear to the thigh), and force on the heel and forefoot sections of the foot are shown during a gait cycle The gait cycle can begin at heel strike. Also shown are the period of engagement for the spring clamp (e.g., from about two to about sixty-two percent gait cycle) and subsequent exoskeleton influence. The same value against time as discussed in the graph set 700 of FIG. 7 can apply to the graph set 1000.

Figure 11A:
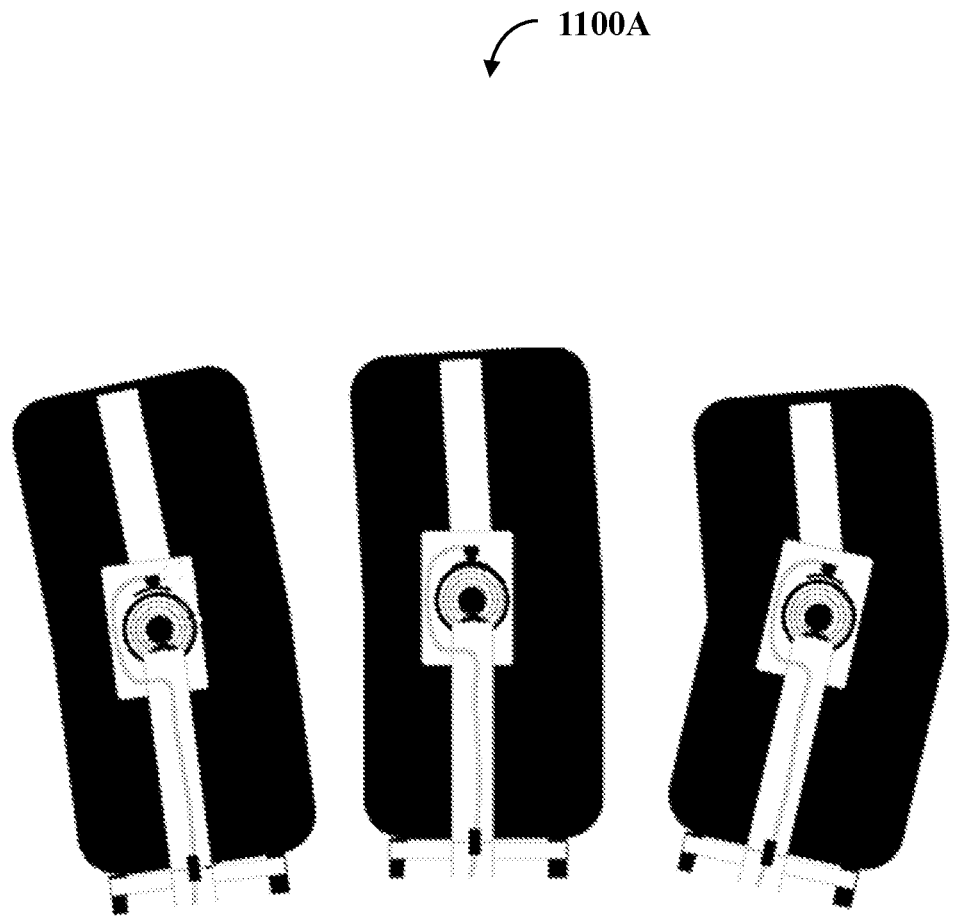
FIG. 11A illustrates a first embodiment of a bend sequence.

FIG. 11A illustrates a first embodiment of a bend sequence 1100A. The spring can physically align with the knee of the wearer. Clamp actuation can occur in response to pressure from the foot. When the foot is off the ground the clamp does not make contact with the spring (housing/arbor depending on embodiment). However, when the foot is on the ground the clamp holds the spring (housing/arbor depending on embodiment). In this embodiment, pressure from bladders under the heel and forefoot apply pressure to a cylinder, pressing a clamp again the spring (housing/arbor depending on embodiment), holding it stationary and allowing energy to be stored and released from/to the spring/exoskeleton brace.

Figure 11B:
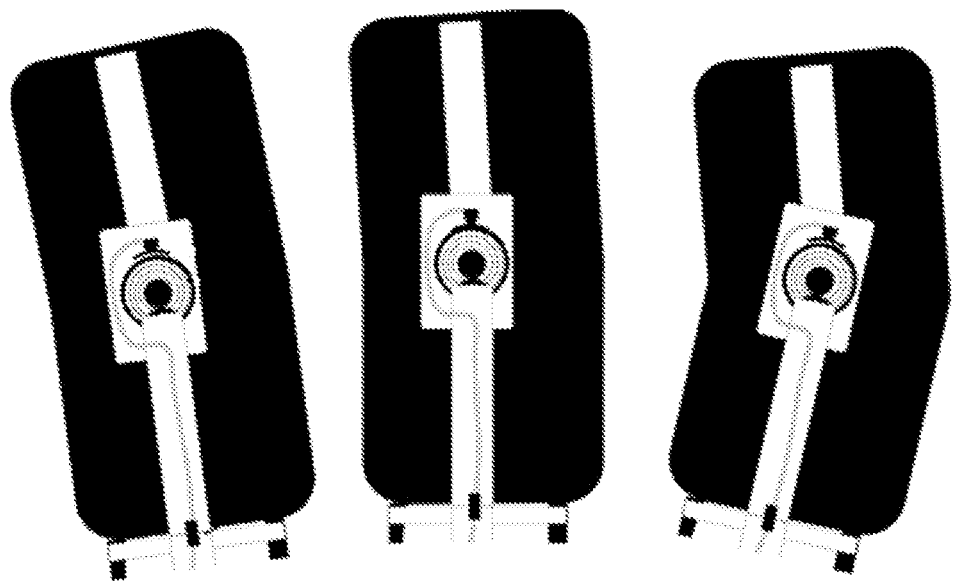
FIG. 11B illustrates a second embodiment of a bend sequence.

FIG. 11B illustrates a second embodiment of a bend sequence 1100B. Similar to with FIG. 9B, the fluid connection can be replaced by an electrical connection. Similarly, the cylinder can be replaced with a solonoid (e.g, the cylinder and/or the solonoic functioning as part of the clamp component). These can be used to clamp the spring (e.g. power spring or torsion spring).

Figure 12:
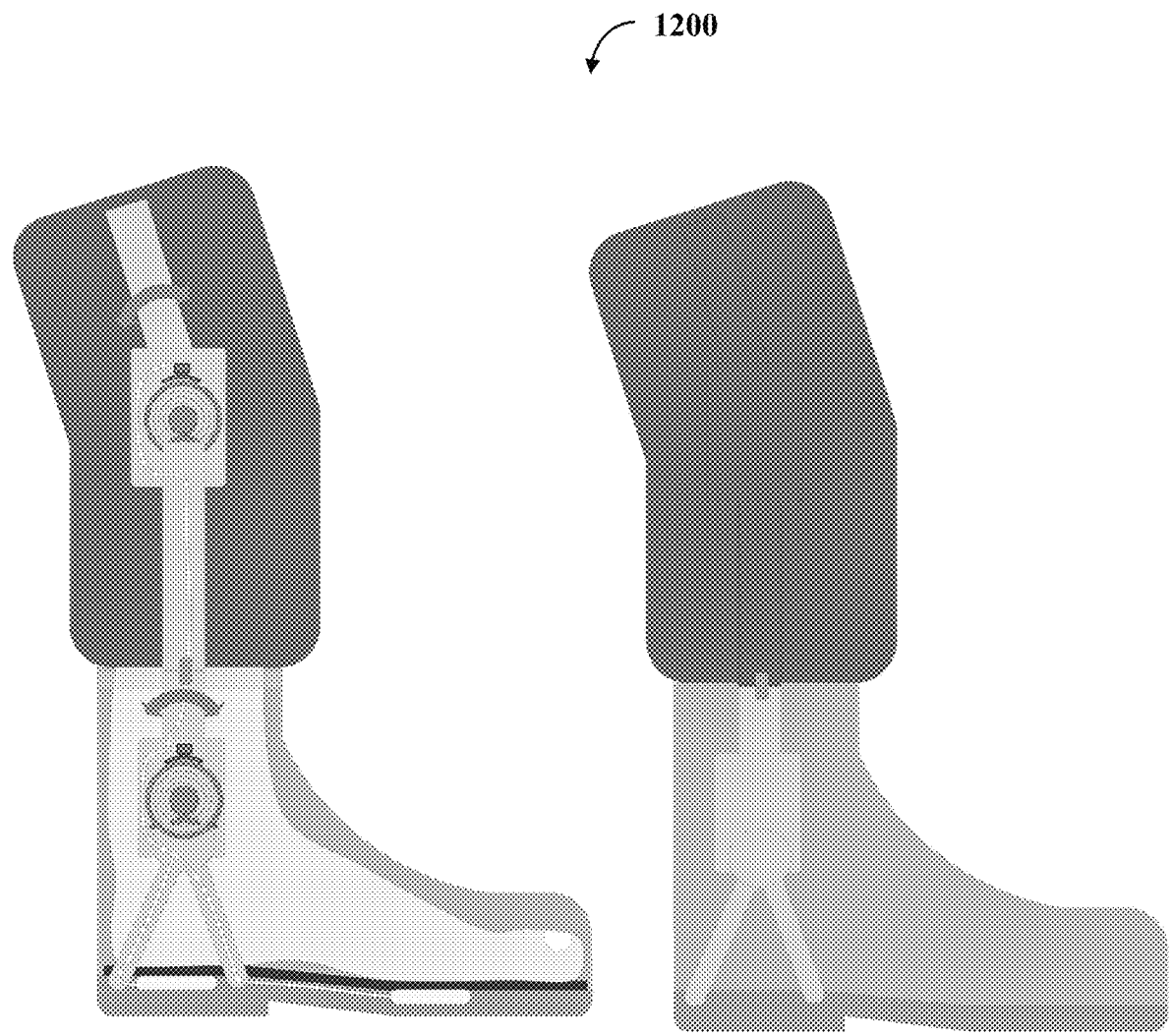
FIG. 12 illustrates one embodiment of an ankle and knee combination exoskeleton configuration.

FIG. 12 illustrates one embodiment of an ankle and knee combination exoskeleton configuration 1200. A human leg could wear multiple springs, such as an ankle spring and knee spring. Connection can be made between the ankle and knee exoskeletons at the top of the boot. The illustration on the left depicts an inner-working view showing the inner components of the exoskeletons. The illustration of the right depicts how the exoskeletons would visually appear in one embodiment. In one embodiment, the boot can work by itself, while the knee or hip braces can be controlled by the boot, with either fluid pressure or electrical signals indicating if the foot is on the ground or not.

Aspects disclosed herein can be practiced to reduce the metabolic rate of a wearer. The metabolic rate is the rate at which the wearer expends energy. The goal is to have the wearer do less work and therefore have a lower metabolic rate.

When pressure is on the foot (the foot made up of a heel and a forefoot (e.g., everything forward of the heel), the spring can be engaged. Otherwise, the spring can rotate like a drum to not add to the metabolic rate during swing phase.

When pressure is on the foot, there can be natural negative work (e.g., when the wearer steps down) and natural positive work (e.g., when the user lifts, propelling themselves forward). The spring can convert the natural negative work into additional positive work and release that additional positive work when the natural positive work is produced. Negative work can be defined, in at least some embodiments, as work that does not propel the body forward while positive work is work that does propel the body forward.

With a wearer's center of mass, the negative work can be when their center of mass is behind the leg (in the direction of travel) and positive work can be when their center of mass is in front of the leg (in the direction of travel). So when the body and forces are opposite this can be considered negative work and when the body and forces are in a unified direction this can be considered positive work.

During the negative work, the exoskeleton 210 of FIG. 2 can function to support the joint, such as the ankle or knee. This can assist the wearer to perform less negative work. This stored work is returned to the joint later in the gait cycle. Therefore, with the return of the stored work when the spring is unwound, amount of positive work with the body performs with the exoskeleton 210 of FIG. 2 is less. Thus, assuming the increase in metabolic rate due to the added weight of the exoskeleton itself it is not prohibitive, overall less work is performed by the wearer and therefore a lower metabolic rate results.

The spring 110 of FIG. 1 can function to wind the spring and therefore return the positive work. One end of the spring 110 of FIG. 1 can couple to a body-side of the exoskeleton 210 of FIG. 2 that aligns with and physically couples to the joint, such as the ankle joint. Another end of the spring 110 of FIG. 1 can couple to an outside-side of the exoskeleton 210 of FIG. 2 that couples to a boot and therefore moves with the foot. This can allow for the spring 110 of FIG. 1 to be wound and in turn unwound to add positive work to the gait cycle. This added work can improve the gait repetition speed that leads to increasing speed, increasing stride length, and improving walking confidence. Aspects disclosed herein can be practiced when one walks on level ground, uneven ground, hilly ground, etc. While designed for gait patterns of FIGS. 7 and 10, since the mechanism is controlled by gait phase (stance and swing), and therefore does not assume a particular gait style (e.g., specific joint angles, specific durations of gait phases, etc.) it can subsequently work for an arbitrary gait pattern.

What is claimed is:

1. A wearable energy system, comprising:
a spring; and
a hip coupling band mechanism configured to couple the spring to a wearer of the spring such that the spring moves with a joint of the wearer,
where the spring is engaged during a stance phase of a gait cycle of the wearer,
where the spring is disengaged during a swing phase of the gait cycle of the wearer,
where the stance phase comprises a first portion and a second portion,
where the second portion follows the first portion in time,
where during the first portion, the spring is wound,
where the joint is a hip joint,
where the first portion comprises a period when flexion occurs for the hip joint, and
where the second portion comprises a period when extension occurs for the hip joint.

* * * * *